(12) United States Patent
Suissa et al.

(10) Patent No.: US 10,918,757 B2
(45) Date of Patent: Feb. 16, 2021

(54) DEVICE AND METHOD FOR DIFFUSING DRY FOG

(71) Applicant: PRESENSIA, Paris (FR)

(72) Inventors: David Suissa, Vincennes (FR); Laurent Martin, Montreuil (FR)

(73) Assignee: PRESENSIA, Paris (FR)

( * ) Notice: Subject to any disclaimer, the term of this patent is extended or adjusted under 35 U.S.C. 154(b) by 830 days.

(21) Appl. No.: 15/118,430

(22) PCT Filed: Feb. 12, 2015

(86) PCT No.: PCT/EP2015/053034
§ 371 (c)(1),
(2) Date: May 7, 2017

(87) PCT Pub. No.: WO2015/121390
PCT Pub. Date: Aug. 20, 2015

(65) Prior Publication Data
US 2017/0246336 A1    Aug. 31, 2017

(30) Foreign Application Priority Data
Feb. 12, 2014 (FR) ........................... 1451102

(51) Int. Cl.
*A61L 9/14* (2006.01)
*B05B 7/00* (2006.01)
(Continued)

(52) U.S. Cl.
CPC ............. *A61L 9/14* (2013.01); *B05B 7/0012* (2013.01); *B05B 7/0075* (2013.01);
(Continued)

(58) Field of Classification Search
CPC . A61L 9/032; A61L 9/122; A61L 9/14; A61L 2209/134; B05B 7/0012;
(Continued)

(56) References Cited

U.S. PATENT DOCUMENTS 3,652,015 A * 3/1972 Beall ................. A61M 16/16
239/338
4,049,200 A    9/1977 Sobol
(Continued)

FOREIGN PATENT DOCUMENTS

EP    0 261 649 A2    3/1988
EP    0 608 176 A1    7/1994
(Continued)

*Primary Examiner* — Cody J Lieuwen
(74) *Attorney, Agent, or Firm* — IM IP Law; Chai Im; C. Andrew Im

(57) ABSTRACT

An anti-condensation housing includes a connector to connect to a diffusing head configured to nebulize a product to diffuse. The housing includes a conduit having an inlet for a nebulized product, an outlet opening at a diffusing end, of the conduit, a fan at an insufflating end of the conduit. The fan generates a flow of air between the insufflating end and the diffusing end of the conduit. An internal surface of the conduit extending along a direction perpendicular to the direction of the air flow creates an obstacle for the progress of the air flow in the conduit. A retainer to retain the nebulized product stopped by the internal surface. A device to diffuse a product implementing the anti-condensation housing and a method for diffusing a product using such a device are provided.

3 Claims, 3 Drawing Sheets

(51) Int. Cl.
*B05B 7/24* (2006.01)
*B05B 7/16* (2006.01)

(52) U.S. Cl.
CPC ............ *B05B 7/0081* (2013.01); *B05B 7/164* (2013.01); *B05B 7/166* (2013.01); *B05B 7/1666* (2013.01); *B05B 7/2424* (2013.01)

(58) Field of Classification Search
CPC ..... B05B 7/0075; B05B 7/0081; B05B 7/164; B05B 7/166; B05B 7/1666; B05B 7/2416; B05B 7/2424; B05B 7/2491
See application file for complete search history.

(56) References Cited

U.S. PATENT DOCUMENTS

| | | | | | |
|---|---|---|---|---|---|
| 4,629,482 | A | * | 12/1986 | Davis | B01D 46/0005 55/385.2 |
| 5,645,769 | A | * | 7/1997 | Tamaru | B01F 3/04007 261/30 |
| 9,126,215 | B1 | * | 9/2015 | Levy | B05B 7/0012 |
| 2008/0223953 | A1 | * | 9/2008 | Tomono | A01M 1/205 239/102.2 |
| 2014/0312136 | A1 | * | 10/2014 | Kubicek | B05B 7/02 239/8 |

FOREIGN PATENT DOCUMENTS

| | | |
|---|---|---|
| FR | 2 870 128 A1 | 11/2005 |
| GB | 525 736 A | 9/1940 |

* cited by examiner

DEVICE AND METHOD FOR DIFFUSING DRY FOG

RELATED APPLICATIONS

This application is a § 371 application from PCT/EP2015/053034 filed Feb. 12, 2015, which claims priority from French Patent Application No. 14 51102 filed Feb. 12, 2014, each of which is herein incorporated by reference in its entirety.

FIELD OF THE INVENTION

The invention relates to a device and a method for diffusing dry fog. The invention is more particularly, but not exclusively, suited for diffusing into a large volume a fragrance aerosol stored in liquid form.

BACKGROUND OF THE INVENTION

According to the prior art, such diffusion is particularly obtained by means of a ventilation circuit with a high flow rate such as an air conditioning system. The fragrance to diffuse takes the form of a liquid in a container comprising a diffusing head that opens out into said ventilation circuit. A compressor makes it possible to inject compressed air in said diffusing head, which takes the fragrance from the container through a Venturi device and nebulizes it in the form of droplets. At the outlet of the diffusing head, in this method of the prior art, the droplets have a diameter ranging from 0.5 μm to 100 μm. The fine droplets are carried by the ventilation flow and the larger ones fall back into the ventilation circuit, where they eventually evaporate under the effect of the same air flow. The air flow rate in such a ventilation or air-conditioning system is greater than the flow rate of nebulized product in a proportion of about $10^7$.

However, when the space in which the product is to be diffused does not comprise a ventilation circuit suitable for generating a sufficiently powerful flow of air, or when the nature of the diffused product does not allow its use in ventilation or air conditioning ducts, nebulization by the diffusing head does not effectively diffuse the product on its own. That is because the proper diffusion of product, particularly a fragrance, is achieved when the nebulized droplets are mostly vaporized, that is to say when said droplets are turned into vapor when they come into contact with a large volume of unsaturated air, and when the non-vaporized droplets are sufficiently fine to remain suspended in the air. For those conditions to be met, the diameter of the droplets diffused must be below 10 μm, which makes it possible to diffuse the product in the form of a fog known as a dry fog. These conditions are not achieved directly at the outlet of the diffusing head.

To make up for that drawback, the devices of the prior art use a chamber, known as a fractionating chamber, which is designed to sort the droplets so as to only allow the finer droplets to be diffused. Document EP 0608176 describes an example of application of such a fractionating chamber. The jet of nebulized fragrance is projected into a chamber that makes it take a path comprising obstacles between the entry of the jet in said chamber and its exit from the fractionating chamber. The impact of the jet moving along in the chamber on the surface of the obstacles makes it possible to concentrate the very large droplets that drip due to gravity along the walls of the chamber. That is because fine droplets tend to bounce off obstacles without wetting them, while larger droplets burst when they come in contact with the obstacle and wet the corresponding wall. The jet is slowed down by the uneven path and its volume is reduced by the process of droplet sorting, and it leaves the chamber for the space in which it is diffused, most often by a small pipe that guides the flow towards an exit at a precise location.

When the aim is to diffuse a product, particularly a fragrance, in a room, particularly in commercial premises, the diffusing system is advantageously placed in a false ceiling. Very often, the resulting dimensional requirements do not allow the installation of a fractionating chamber adequate for effectively sorting the droplets, but they do however slow the flow significantly. Indeed, the effectiveness of the device makes it necessary for the jet to be discharged vertically. The height of the bottle containing the product to diffuse is about 30 cm and the space above the false ceiling generally ranges from 40 cm to 1 meter, leaving little room for installing a fractionating chamber. Further, the direction of diffusion of the product in the space, downward when the device is installed in a false ceiling, makes the management of the flow of the droplets intercepted by the obstacles of the fractionating chamber more complex. That has several drawbacks, including the following:

- drops of diffused product condense at the outlet of the pipe or at the outlet of the diffusing head. A drop eventually falls on a surface close to the outlet, in the space in which the product is to be diffused, where said drop soils the floors, walls or objects present in the space;
- the diffused product condenses inside the outlet pipe, harming the quality of diffusion, as the fog then passes through a volume of liquid fragrance;
- the slow speed of the fluid at the outlet leads to the poor homogenization of the product diffused in the space, leading, for example, to excessively high or even inconveniencing olfactory perception close to the diffuser, and none in spaces located further away;
- the fog at the outlet of the diffuser is thick and very visible, making people in the area feel fairly anxious, and contaminating the objects in the nearby environment.

Document EP 0 261 649 describes a device for diffusing dry fog that uses a set of blades before the nebulizer, which blades have the technical effect and the same drawbacks as a fractionating chamber.

OBJECT AND SUMMARY OF THE INVENTION

The invention aims to remedy the drawbacks of the prior art and therefore relates to a housing known as an anti-condensation housing, comprising means for connection to a diffusing head suitable for nebulizing a product to diffuse, characterized in that it comprises:

a. a conduit comprising, between a diffusing end and an insufflating end, an inlet for a nebulized product;
b. an outlet opening at the diffusing end of said conduit;
c. a fan at the insufflating end of said conduit, to generate a flow of air between said end and the diffusing end of the conduit;
d. an internal surface of said conduit, located between the inlet for the nebulized product and the diffusing end, which surface extends along a direction perpendicular to the direction of the air flow so as to create an obstacle for the progress of the flow in the conduit;
e. means for retaining the nebulized product stopped by said internal surface.

Thus, the creation of an air flow and the transport of nebulized product in that air flow over a definite distance allows the total or partial evaporation of the product in said air flow and in any case the production of dry fog at the outlet. The largest drops of product are stopped by the internal surface and are collected in said conduit, where they evaporate gradually under the effect of said air flow. The length of the conduit is determined on the basis of the type of product to diffuse, the characteristics of the nebulization and the air flow insufflated. Depending on the embodiment, the internal surface of the conduit suitable for creating an obstacle for the progress is made up of the very wall of the conduit formed like a bend, a boss or a raised fold inside said conduit or an added element such as a baffle inside said conduit, without the list being exhaustive. The height, location and progressivity of the obstacle make it possible to recover the drops of product that are out of size depending on the characteristics of diffusion, while limiting head loss.

The invention can be implemented advantageously in the embodiments described below, which may be considered individually or in any technically operative combination.

Advantageously, the means for generating the air flow consist in a silent electric fan. Such a fan is easy to control and allows the product to be diffused unobtrusively from the sound viewpoint. The electricity requirements of such a fan are very low, even though the air flow generated is sufficient to make the product evaporate, particularly the product collected in the retaining means.

The conduit may have any section, circular, rectangular or elliptical, but these configurations are not limitative.

Advantageously, the diameter of the circle that fits in the section of the conduit ranges between 60 mm and 120 mm. Thus, the mist of nebulized product in the conduit has sufficient distance to be carried by the air flow before it hits a wall of the conduit at the time of nebulization.

Advantageously, the length of the conduit between the insufflating end and the diffusing end ranges between 3 and 10 times the diameter of the circle that fits within the section of the conduit. Thus, said conduit is sufficiently long to obtain dry fog, but remains sufficiently compact for discreet installation, particularly in a false ceiling.

In an advantageous embodiment of the anti-condensation housing according to the invention, the conduit is bent between the insufflating end and the diffusing end. Thus, the direction of ejection of the air and product flow is not constrained by the direction of the nebulized jet in the conduit. There is no longer any need to use a pipe to direct the flow, which removes the known risks of condensation of the prior art. In this embodiment, the bend also makes the internal surface stop the larger drops of nebulized product as they progress through the conduit.

In this last embodiment, the conduit comprises two parts that can be directed one in relation to the other. Thus, the direction of ejection of the air and product flow is adjustable depending on the installation of the diffusion device.

Advantageously, the conduit comprises:
f. a baffle between the inlet for nebulized product and the diffusing end.

Said baffle stops the largest drops of nebulized product and thus allows a shorter conduit, or, with the same length of conduit, allows greater homogeneity of the diffused product. Depending on the direction of the conduit, said baffle also makes it possible to avoid projecting the largest drops on the walls of the conduit, where they could drop and fall in the diffusion space.

Throughout this document, the term "baffle" refers to a localized obstacle that deviates the flow of air and product.

Advantageously, said baffle cooperates with the wall of the conduit to create a retention zone. The product retained in that zone is exposed to the air flow and evaporates. Thus, the totality of the nebulized product is used and conduit fouling is reduced.

In one alternative embodiment of the housing according to the invention, said housing comprises:
g. a container that communicates with the retention means.

Thus, the product stopped by the baffle or the shape of the wall of the conduit, contained in the retention means and not vaporized by the air flow, flows into said container where it is collected.

Advantageously, the anti-condensation housing according to the invention comprises:
h. means for heating the air flow generated at the insufflating end.

Thus, the flow is heated to the optimal temperature for diffusing the product, regardless of the environment in which the diffusion takes place.

The invention also relates to a device for diffusing a product in the form of a dry fog, which device comprises a diffusing assembly comprising:
i. a bottle containing the product to nebulize;
ii. a diffusing head, which is connected to the bottle and comprises a compressed air inlet;
iii. an anti-condensation housing according to the invention, wherein the nebulized product inlet is connected to the diffusing head.

This diffusing device is independent and makes it possible to diffuse the product, particularly fragrance, without the drawbacks of the prior art, in the absence of a ventilation or air conditioning circuit.

Advantageously, the diffusing head of the diffusing device according to the invention comprises adjustable means to limit the flow of compressed air injected into said diffusing head. Thus, the quantity of product diffused at each nebulization is finely adjusted depending on the environment in which the product is diffused. The device according to the invention can thus be used with all sources of compressed air, particularly an industrial network when it is available.

In an advantageous embodiment, the diffusing device according to the invention comprises:
iv. means to heat the bottle containing the product to nebulize.

Thus, when the device according to the invention is installed in a cold environment, such as a car park in winter, the product is advantageously heated to a temperature suitable for obtaining good nebulization.

Advantageously, the device according to the invention comprises:
v. means suitable for indicating the level of product remaining in the bottle.

Thus, the means make it possible to measure the consumption of product and foresee the maintenance and filling operations.

Advantageously, the conduit of the diffusing assembly of the device according to the invention comprises fastening means for suspending said conduit and bottle. Thus, each independent diffusing assembly is easily installed in the space into which the product is diffused, such as a false ceiling.

In one particular embodiment, the device according to the invention comprises:
vi. a casing comprising a hatch with a lock, and an opening that communicates with the diffusing end of the conduit of the anti-condensation housing.

Thus, the device according to the invention is easily concealed in the space in which the product is diffused and protected from malicious damage, while allowing access to authorized personnel, particularly for changing or filling the bottle.

Advantageously, the device according to the invention comprises:

vii. a pump unit suitable for delivering compressed air to the diffusing head of the diffusing assembly.

Thus, the device is independent, including for the generation of compressed air. The use of a dedicated pump unit makes it possible to control and finely manage the product diffusion parameters.

In this last embodiment, the diffusing device according to the invention comprises:

viii. means for drying the compressed air produced by the pump unit.

Thus, the air injected in the diffusing head is dry, which is favorable to the nebulization of the product into evenly-sized drops, and avoids the problem of the condensation of exogenous products such as oil or water in the conduit of the anti-condensation housing, or the contamination of the product diffused by such exogenous products.

In an advantageous embodiment, the diffusing device according to the invention comprises a plurality of diffusing assemblies supplied with compressed air by a single pump unit and comprising:

ix. a unit for distributing the flow of compressed air between the different diffusing assemblies;

x. means for adjusting the overall pressure of the compressed air circuit.

Thus, the diffusing assemblies are distributed efficiently in the volume of the space in which the diffusion is to be carried out. The powerful pump unit is installed at a distance in order to not generate noise and the cooperation of the means for distributing the flow, the means for adjusting the overall pressure and the means for limiting the flow from each diffusing head makes it possible to adjust the quantity of diffused product very precisely at each point of diffusion, while allowing noiseless operation.

The invention also relates to a method for diffusing a product in the form of dry fog in a diffusion space, which method uses the diffusing device according to the invention for that purpose and comprises the steps of:

u. injecting compressed air into a diffusing head, so as to generate the nebulization of a volume of product in the conduit of a diffusing assembly;

w. simultaneously controlling the means for generating the air flow at the insufflating end of said conduit so as to generate a flow of air that is greater than 10,000 times the flow of nebulized product.

Thus, the method according to the invention controls both the injection of the product to diffuse and the air flow, so as to obtain an optimal result in terms of diffusion in relation to the desired effect. Compared to the diffusion methods of the prior art, particularly the method consisting in nebulizing the product in a ventilation duct, the method according to the invention is not constrained by the air flow from said ventilation, and thus makes it possible to consume far less product to diffuse for an equivalent result.

Advantageously, the method according to the invention comprises, after step (w), a step of:

x. continuing to insufflate air in the conduit after the end of product nebulization.

Thus, the drops of product retained in the conduit of the diffusing assembly evaporate under the effect of that air flow.

Advantageously, the method according to the invention comprises before steps (u) and (w) the steps of:

y. spatially distributing the diffusing assemblies in the diffusion space;

z. calibrating the pressure of the compressed air injected in step (u) in each diffusing assembly installed so as to evenly distribute the diffused product in the diffusion space.

Thus, the distribution of the diffused product in the diffusion space is perfectly controlled.

In an exemplary embodiment of the method according to the invention, the flow of air insufflated in steps (w) and (x) ranges between 20 and 80 m$^3$/hour ($5.5 \times 10^{-3}$ m$^3$s$^{-1}$ to $22 \times 10^{-3}$ m$^3$s$^{-1}$) preferably about 35 m$^3$/hour ($10^{-2}$ m$^3$s$^{-1}$). Thus, compared to the prior art, the flow of insufflated air is, by order of magnitude, 1000 times smaller than when the product is diffused in a ventilation duct, but also about 1000 times greater than when the product is diffused by means of a fractionating chamber according to the prior art, which allows the creation of dry fog and the effective diffusion of the product.

In an exemplary embodiment of the method according to the invention that is compatible with the previous one, the compressed air pressure injected into the diffusing head ranges between 0.3 bar and 1.5 bar ($0.3 \times 10^5$ Pa and $1.5 \times 10^5$ Pa), preferably about 0.6 bar ($0.6 \times 10^5$ Pa). Such low-pressure injection particularly makes it possible to reduce the noise of nebulization and finely control the quantity of nebulized product in the anti-condensation housing of the device according to the invention.

BRIEF DESCRIPTION OF THE DRAWINGS

The invention is described below in its preferred embodiments, which are not limitative in any way, and by reference to FIGS. 1 to 7, wherein.

DETAILED DESCRIPTION OF THE EMBODIMENTS

Throughout this document, the term 'vapor' refers to the gaseous phase of a compound. The term "dry fog" refers to a two-phase mixture of the gaseous and liquid phases, where the liquid phases are in the form of micro droplets with a diameter that is sufficiently small to allow them to bounce off solid surfaces without wetting said surfaces.

Figure 1:
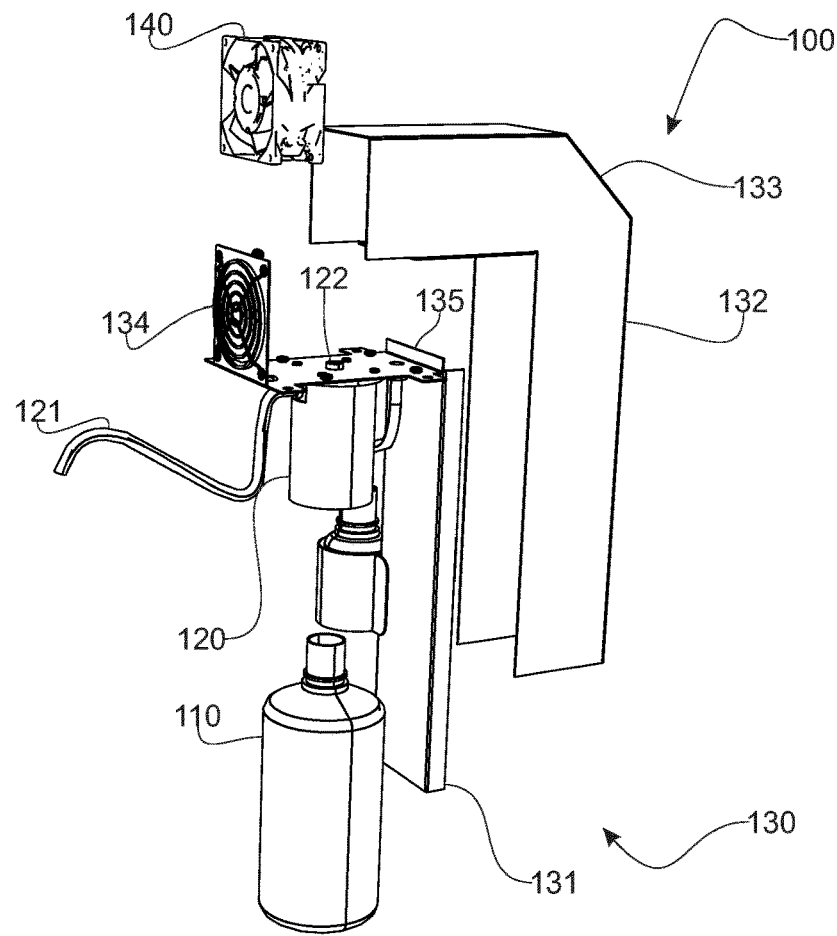
FIG. 1 is a perspective exploded view of the front and right-hand side of an exemplary embodiment of a diffusing assembly according to the invention.

In FIG. 1 of an exemplary embodiment, the diffusing assembly (100) according to the invention comprises a bottle (110) of the product to diffuse, the neck of which is introduced in a diffusing head (120) that communicate with the inside of said bottle. The invention relates more particularly to the diffusion of fragrances, so that the product contained in the bottle (110) is more generally a fragrance or an essential oil. However, the invention is also suitable for diffusing other products, particularly products for disinfecting, neutralizing odors, humidification, diffusing repellents or insecticides and generally diffusing a product in the form of an aerosol. The diffusing head (120) is connected to a compressed air inlet (121), for example in the form of a hose. That diffusing head comprises a nebulizing nozzle, which communicates with the inside of the conduit of an anti-condensation housing (130) using appropriate means (122), generally a tube, which may be rigid or flexible. Said anti-condensation housing (130) comprises a conduit which, in this exemplary embodiment, has a rectangular section and is made up of an assembly of bent welded plates (131, 132). The end (134) of the conduit that is proximal to the nebulized product inlet (122), comprises means (140) for generating a flow of air, for example an electric fan (140) known as a silent fan. Such a fan is commonly used in applications such as the ventilation of electrical cabinets. As a non-limitative example, said fan has a diameter of 80 mm, and its output is approximately 40 m$^3$/h with an electricity rating of about 3 W. Said fan is supplied by a very low voltage line (not shown) with 12V or 24V power. In a particular embodiment, an electric resistance heater (not shown) powered by the same current as the fan is placed in the air flow immediately after said fan (140) in order to heat said air flow to a temperature of about 30° C. This temperature improves the diffusion of fragrances without denaturing them.

In this exemplary embodiment, the conduit has a rectangular section and is bent to 90°, with a small curvature radius, so as to reduce its dimension for an equal length. Advantageously, in this exemplary embodiment, the bending position is selected so that the conduit surrounds the bottle (110) and makes it possible to direct the jet downward when said bottle is in vertical position. This embodiment is thus particularly compact and suitable for use where the device according to the invention is concealed in a false ceiling.

The section of the conduit is determined by the nebulization jet opening into said conduit. That is because if the height of the conduit opposite that inlet is too small, the aerosol created during nebulization tends to condensate on the wall opposite said product inlet. As a non-limitative example, the height of said conduit for diffusing a fragrance is approximately 10 cm and generally ranges between 5 cm and 15 cm. The length of the conduit is selected to obtain dry fog at its outlet. Said length is determined, for example, by means of testing depending on the nebulized product. As a non-limitative example, the total length of the conduit ranges from 3 to 10 times the diameter of the circle that fits within the section of the conduit.

Figure 7:
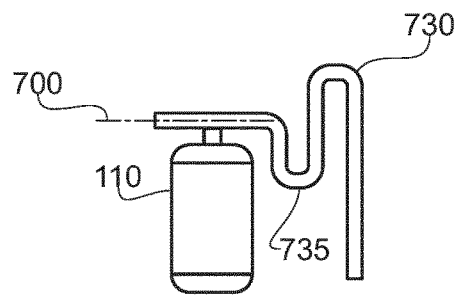
FIG. 7 is a side view of an exemplary embodiment of the device according to the invention comprising a conduit with a double bend.

In FIG. 7 of an exemplary embodiment, the conduit (730) of the device according to the invention comprises a double bend, so that said conduit (730) comprises surfaces that extend substantially perpendicular to the original direction (700) of the air flow, which thus create obstacles for the progress of said flow. The largest droplets are projected against the walls of the conduit at the bends, where they flow towards a retention zone (735). In this exemplary embodiment, the bends are made around axes that are substantially perpendicular to the initial direction (700) of the air flow, with curvature radiuses that are about the same as the diameter of the conduit. An equivalent result is obtained by one or more bends along an axis parallel to that initial direction (700) of the air flow, with tighter curvature radiuses. Similarly, while the conduit is directed so that the flow of air is directed downward at the diffusing end in this exemplary embodiment, the conduit is directed for diffusion in the upward direction in other embodiments, or horizontal or any other direction suitable for the configuration of the installation comprising such a device. In other exemplary embodiments, the bends thus made have an angle that is smaller than or greater than 90°.

Returning to FIG. 1, in this exemplary embodiment, when the nebulized product is introduced in the conduit through the inlet (122) that opens into the anti-condensation housing, and the product thus nebulized is carried by the flow of air produced by the fan (140), the largest drops, for example those with a diameter above 10 μm ($10 \times 10^{-6}$ m) would be projected against the bent part (133) of the conduit. However, depending on the mode of installation of that diffusing assembly, the drops thus projected on the bent part (133) of the conduit would be liable to flow along the walls of said conduit and fall through the diffusing end. In order to avoid such a situation, the diffusing assembly according to the invention comprises, in the conduit, a baffle (135) that cooperates with the walls of the conduit in order to create a zone for retaining drops of nebulized product caught by said baffle (135). The presence of such a baffle (135) is not limited to this type of conduit. The height of the baffle is adapted depending on its position in the conduit so as to intercept the larger droplets and let the finer droplets through, particularly when their diameter is below 10 μm. The term 'baffle' refers to an obstacle located in the conduit, which obstacle is suitable for deviating the progress of the gas flow in said conduit. In non-exhaustive exemplary embodiments, such a baffle is obtained by adding a plate fixed to the inside of the conduit by any means such as welding, soldering or riveting or takes the form of a rib made of the conduit material by bending or molding.

Figure 2:
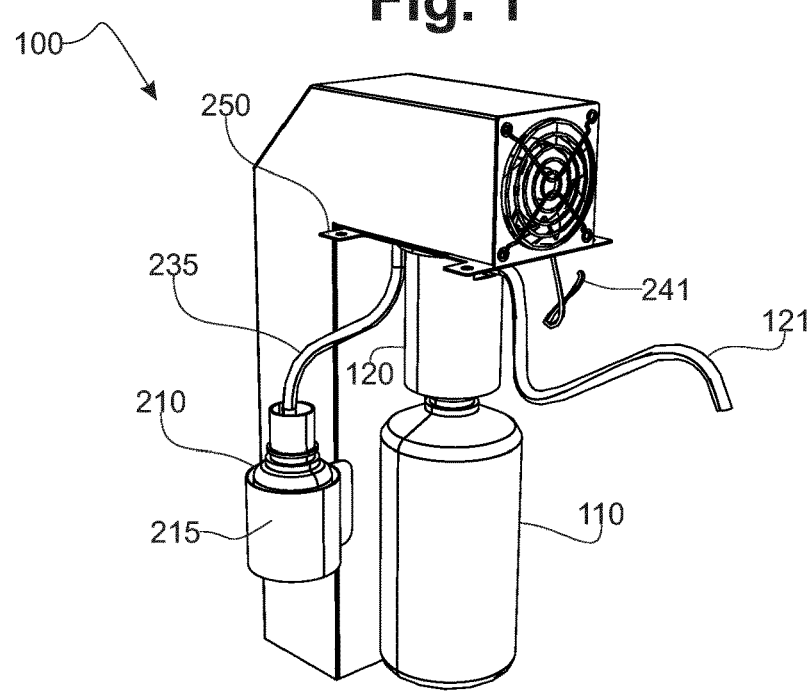
FIG. 2 is a perspective view of the front and left-hand side of the assembly in FIG. 1.

In FIG. 2 of this exemplary embodiment of the diffusing assembly according to the invention, the retention zone is demarcated by the baffle in the conduit and communicates with a container (210), for example by means of a hose (235). In this exemplary embodiment, said container (210) is connected to the anti-condensation housing by a support (215) fixed to a wall of the conduit. Another wall of the conduit advantageously comprises fastening tabs (250) for suspending said anti-condensation housing. Thus, in this exemplary embodiment, the diffusing assembly (100) according to the invention forms a compact whole where all the means are connected to the diffusing conduit. In order to make the assembly operate, it merely needs a connection (121) to a source of compressed air, and an electrical connection (241) for the fan.

Figure 3:
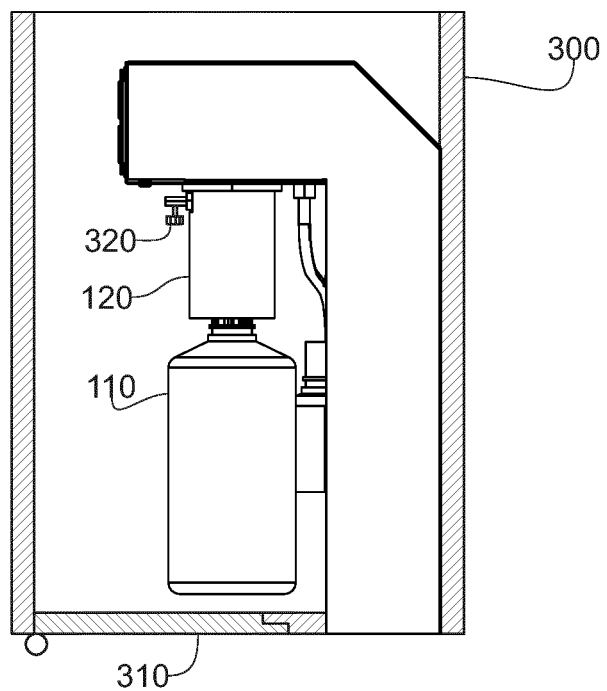
FIG. 3 is a right-hand view of the installation of a diffusing assembly according to the invention in a casing, a section of which is represented in this view.

In FIG. 3, the diffusing assembly according to the invention is advantageously placed in a casing (300) comprising a hatch (310) to allow access to the bottle (110) for refilling or changing it when all the product has been consumed.

To that end, the bottle advantageously comprises a visual or electronic level indicator (not shown) to allow a maintenance operator to detect the need for replacement or refilling. In this exemplary embodiment, said casing (300) is designed for installing the diffusing assembly to the ceiling. In that situation, said hatch (310) also allows access to the device for maintenance purposes. The compressed air inlet in the diffusing head (120) advantageously comprises a means (320) to adjust the injected air flow. The adjustment of the flow determines the quantity of product taken in by Venturi effect in the bottle (110) and therefore the quantity of product nebulized in the anti-condensation housing. In this exemplary embodiment, the means (320) for adjusting the flow is manual. Alternatively, the means may be remotely controlled electronic means.

Figure 4:
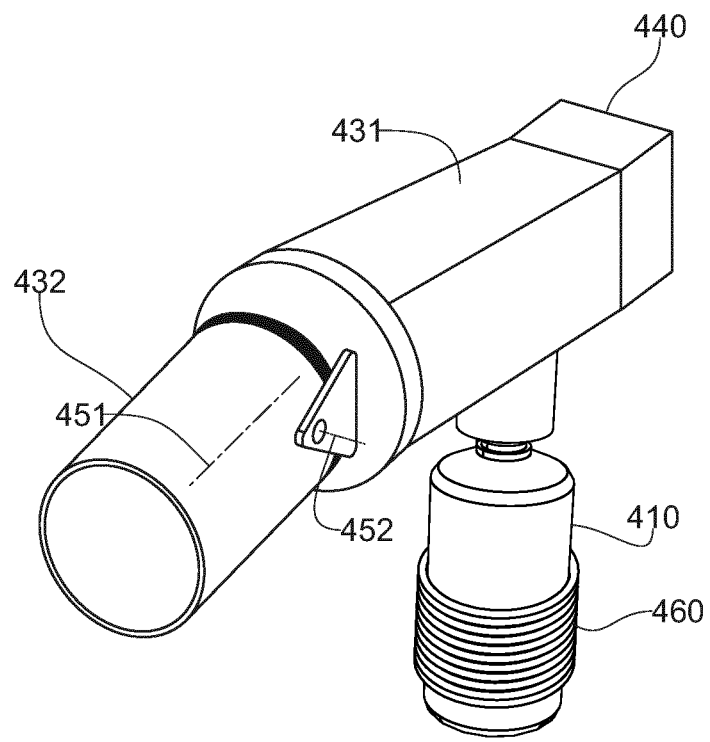
FIG. 4 is a perspective view of another embodiment of the diffusing assembly according to the invention, where the conduit comprises a part that can be turned.

In FIG. 4 of another exemplary embodiment of the diffusing assembly according to the invention, the conduit of the assembly comprises two parts (431, 432) that can be turned in relation to each other, here along two pivot links with perpendicular axes (451, 452). Thus, the part (432) comprising the diffusing end of the conduit can be turned in order to optimize the direction of the diffusion flow in relation to the environment in which that diffusing assembly is located. In this exemplary embodiment, the fan (440) is connected to the fixed part (431) of the conduit, which is also connected to the bottle (410) containing the product to diffuse. In one particular embodiment (not shown), the mobile part (432) is turned in relation to the fixed part (431) of the conduit by means of remotely controlled powering means.

In a non-specific implementation of that last embodiment, the diffusing assembly according to the invention comprises means (460) to heat the bottle (410) of product to diffuse. In that non-exclusive exemplary embodiment, said heating means consists in resistance heater (460) suitable for heating the bottle from the outside. Other heating modes are possible from outside the bottle or directly in the product. Thus, when the diffusing assembly according to the invention is used in a cold environment, those heating means (460) make it possible to heat the diffused product to the conditions of viscosity that are favorable for nebulization. Depending on the nature of the product diffused, the heating means also make it possible to favor the vaporization of the product when it passes through the diffusing head.

Figure 5:
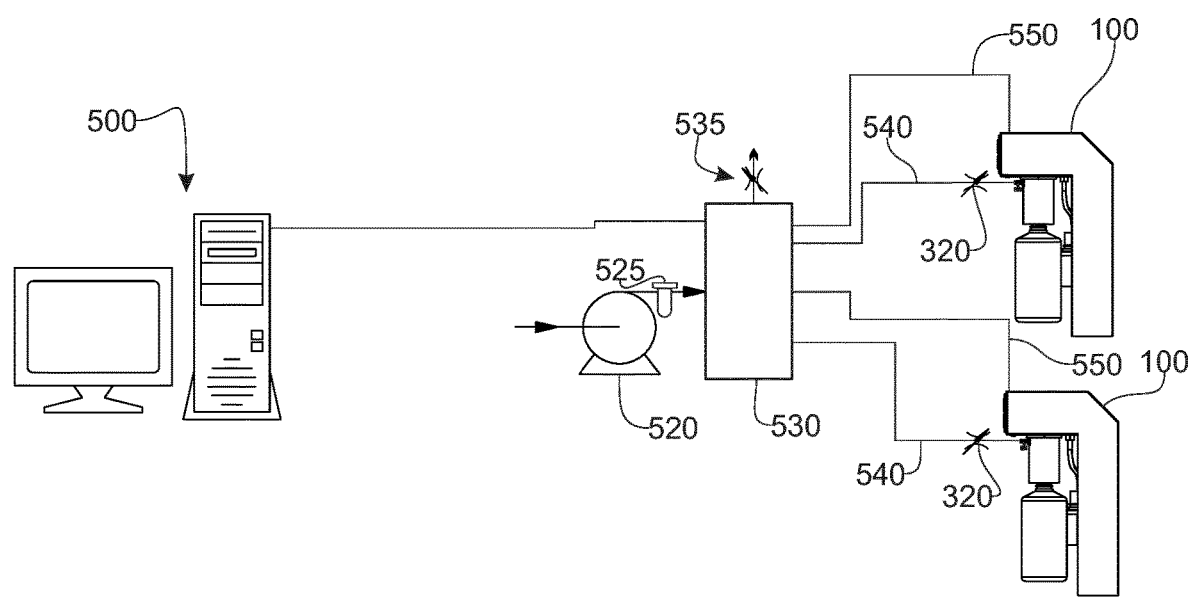
FIG. 5 is a schematic representation of an exemplary embodiment of a diffusing device according to the invention, comprising a plurality of diffusion assemblies connected to a single pump unit.

In FIG. 5 of an exemplary embodiment of the diffusing device according to the invention, particularly suitable for diffusion in a large volume, said device comprises a plurality of diffusing assemblies (100) supplied with compressed air by a single pump unit (520). In alternative embodiments, said pump unit (520) is made up of a piston compressor, a screw compressor or any other device suitable for producing compressed air, associated or otherwise with a buffer capacity and advantageously made up of a diaphragm compressor or oscillating piston compressor operating without oil. At the outlet of the pump unit (520), the compressed air is directed to a distributing unit (530), after passing through a filter or an oil separator and dryer (525). Said compressed air distribution unit (530) comprises a pressure regulator (535) that is adjusted manually or electronically controlled, which makes it possible to adapt the pressure from the pump unit, generally 8 bars, to the number of diffusing assemblies (100) supplied, for example by creating a leak. Thus, regardless of the number of diffusing assemblies (100) connected, the pump (520) always operates in favorable conditions, which prevents premature wear and tear and reduces noise.

In this embodiment, supervising and controlling means (500) make it possible to control the distribution unit (530) or the pump unit and thus program, for each diffusing assembly (100), the nebulization time, the quantity of product nebulized and the time frequency of the diffusion depending on the characteristics of the space into which the product is diffused. The compressed air is injected in the diffusing heads under pressure of about 0.6 bar, more generally from 0.3 bar to 1.5 bar depending on the diffused product and the result sought. In one exemplary embodiment, the distribution unit (530) controls the sending of compressed air in the piping (540) connecting said unit (530) to the diffusing assemblies (100). In another exemplary embodiment, the distribution unit also controls the starting up and stopping of the fans of diffusing assemblies. In this last exemplary embodiment, the distribution unit is connected to each diffusing assembly (100) by a pneumatic link (540) and by an electrical connection (550) supplying very low voltage.

The diffusion assemblies (100) are distributed in the space in which the product is to be diffused. That distribution is obtained by means of tests or simulations. Such tests or simulations prior to the implementation of the device according to the invention also make it possible to define the time frequency of nebulization and volume of product thus nebulized. The volume of nebulized product depends on the calibration of the pressure and air flow injected in the diffusing heads of the diffusing assemblies (100). These adjustments are made, firstly, by means of a pressure regulator (535) and secondly, by means of individual adjusting devices (320), shown here schematically, of each diffusing assembly (100).

In one exemplary embodiment, when the diffusing device only comprises one diffusing assembly, the use of a distributing unit is not necessary. The pressure regulator is installed at the outlet of the pump unit and the supervision means (500) directly control the pump unit and the fan of said diffusing assembly (100).

Figure 6:
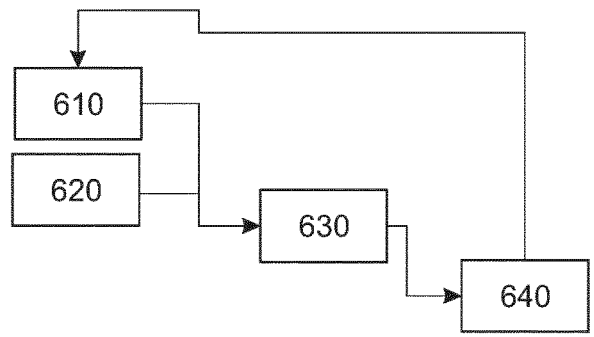
FIG. 6 is a logical diagram of an exemplary embodiment of the method according to the invention.

In FIG. 6 of an exemplary embodiment, the method according to the invention comprises, on the scale of one diffusing assembly, a first controlled injection step (610) consisting in injecting compressed air under suitable pressure into the diffusion head of said diffusion assembly. This step is managed by supervision means that control the distribution unit or directly the pump unit. Simultaneously with the injection step, a ventilation step (620) consists in controlling the starting up of the fan of the diffusing assembly. Depending on the product diffused and the conditions of implementation, that ventilation step (620) is absolutely simultaneous with nebulization or pre-triggered before nebulization or triggered after a given delay following said nebulization. In a step (630) known as the post-ventilation step of the method according to the invention, ventilation is continued after the nebulization step is completed. Depending on the nature of the ventilating means, the post-ventilation step (630) is carried out with an air flow rate identical to that in the ventilation step (620) or a different flow rate. Further, when the diffusing assembly has means for heating the air flow, the temperature of that air flow is also controlled during those two steps (620, 630). That is because the ventilation step (620) is aimed at creating a flow of dry fog from a cloud of product nebulized in the anti-condensation housing, whereas the post-ventilation step (630) is aimed at making the drops of products deposited on the walls of the conduit during the previous steps evaporate, and the conditions of ventilation and heating corresponding to those two steps (620, 630) are specifically suitable for the purpose sought. After a delay step (640) specific to each controlled diffusing assembly, the process is repeated.

The description above and the exemplary embodiments show that the invention achieves its objectives; in particular, the device and method according to the invention make it possible to diffuse a product optimally and in a controlled manner in a space, regardless of the volume of the space, and depending on the embodiment, by the individual control of said assemblies by centralized means. More precisely, the device according to the invention particularly makes it possible:

to adapt the quantity of product diffused by each diffusing assembly;

to make up for the head loss differences relating to the difference in length of compressed air pipes between each diffusing assembly and balance those head losses by the individual adjustments of each diffusing head.

The anti-condensation housing according to the invention makes it possible:

- to dilute the fog of product in a larger volume of dry air;
- to make it easier for the product to evaporate before it leaves the conduit and be diffused in the space in which the product is to be diffused;
- to improve the fineness of the fog diffused in an overall compact volume;
- to retain the drops of liquid formed at the exit of the diffusing head;
- to recover the surplus liquid product that collects at the outlet of the diffusing head and avoid contamination;
- to guide the flow of air and product towards specific zones of the diffusion volume;
- to increase the speed of flow of the air and product and thus improve the distribution of product in the volume of diffusion.

Thus, the method and the device according to the invention offer their user the following benefits:

- making the fog virtually invisible;
- making it possible to install the diffusion assembly in a small area that is removed from the diffusion zone;
- obtaining more even diffusion, particularly a more even olfactory sensation when the product diffused is fragrance;
- limiting the contamination of surrounding surfaces thanks to the absence of liquid drops.

The invention claimed is:

1. An anti-condensation housing, comprising:
a bottle containing a product to be nebulized;
a diffusing head connected to a compressed air inlet communicating with an inside of the bottle to nebulize the product;
a tube comprising a diffusing end, an insufflating end, a bent portion at 90° between the diffusing end and the insufflating end, wherein the, tube has a section with an inscribed circle with a diameter between 60 mm and 120 mm, the section of the tube being continuous and forming a single flow path from the insufflating end to the diffusing end, and over a length between 3 and 10 times the diameter of the inscribed circle, a bending position is configured such that the tube surrounds the bottle and directs an airflow downward at the diffusing head when the bottle is in a vertical position, and a connector to connect the diffusing head to a nebulized product inlet between the diffusing end and insufflating end;
wherein the compressed air inlet is independent from the tube;
an outlet opening at the diffusing end of the tube;
a fan at the insufflating end of the tube, the fan generates an air flow at a flow rate of at least 35 m$^3$ per hour between the insufflating end and the diffusing end of the tube;
a baffle inside the tube, located between the nebulized product inlet and the diffusing end, upstream of the bending position with respect to the air flow, the baffle extending along a direction perpendicular to a direction of the air flow in the tube to provide an obstacle for a progress of the air flow in the tube between the nebulized product inlet and the bent portion, and a height of the baffle is configured to intercept large droplets of the product with a diameter equal to or above 10 µm and to permit droplets with the diameter below 10 µm to go through; and
the baffle cooperates with a wall of the tube to create a retention zone in the conduit to retain a nebulized product stopped by the baffle.

2. The anti-condensation housing according to claim 1, further comprising a container in communication with the retention zone.

3. The anti-condensation housing according to claim 1, further comprising a heater to heat the air flow generated at the insufflating end.

* * * * *